United States Patent [19]

Stuke

[11] Patent Number: 4,686,366
[45] Date of Patent: Aug. 11, 1987

[54] LASER MASS SPECTROMETER

[75] Inventor: Michael Stuke, Goettingen, Fed. Rep. of Germany

[73] Assignee: Max-Planck-Gesellschaft zur Foerderung der Wissenschaften e.V., Fed. Rep. of Germany

[21] Appl. No.: 800,546

[22] Filed: Nov. 21, 1985

[30] Foreign Application Priority Data

May 15, 1985 [DE] Fed. Rep. of Germany ....... 3517667

[51] Int. Cl.$^4$ .............................................. B01D 59/44
[52] U.S. Cl. .................................. 250/287; 250/288; 250/423 P
[58] Field of Search ............... 250/281, 282, 283, 288, 250/287, 423 P

[56] References Cited

U.S. PATENT DOCUMENTS

| 2,720,593 | 10/1955 | Richards et al. | 250/287 |
| 2,758,214 | 8/1956 | Glenn | 250/287 |
| 4,204,117 | 5/1980 | Aberle et al. | 250/423 P |
| 4,532,219 | 7/1985 | Hagen et al. | 250/288 |

OTHER PUBLICATIONS

Ultrasensitive Fingerprint Detection of Organometallic Compounds by Laser by Michael Stuke, published Appl. Phys. Lett. 45(11), Dec. 1, 1984.

Primary Examiner—Bruce C. Anderson
Attorney, Agent, or Firm—Handal & Morofsky

[57] ABSTRACT

A laser mass spectrometer comprises an electrode system and an ion detector system supported on a mounting flange. The electrode system defines an ionization space, an ion acceleration space and a time-of-flight or separation path. At least some of the electrode of the electrode system are removably mounted on support rods extending an axial or ion path direction, to allow accomodation of the distance between the ionization space and the mounting flange to the configuration of an apparatus or vacuum system with which the mass spectrometer is used. Thus, the distance between the mounting flange and the ionization space may be varied by using separation path of different length. The ionization is effected by laser radiation, which may be coupled in through a window in the mounting flange. To derive additional information about a substance under investigation, means may be provided for coupling out radiation emitted by the ionized substance in the ionization space, and the laser may provide radiation pulses having a length in the order of picoseconds, as 10 ps and less, to avoid fragmentation of larger molecules which would prevent detection of the "parent ion".

16 Claims, 6 Drawing Figures

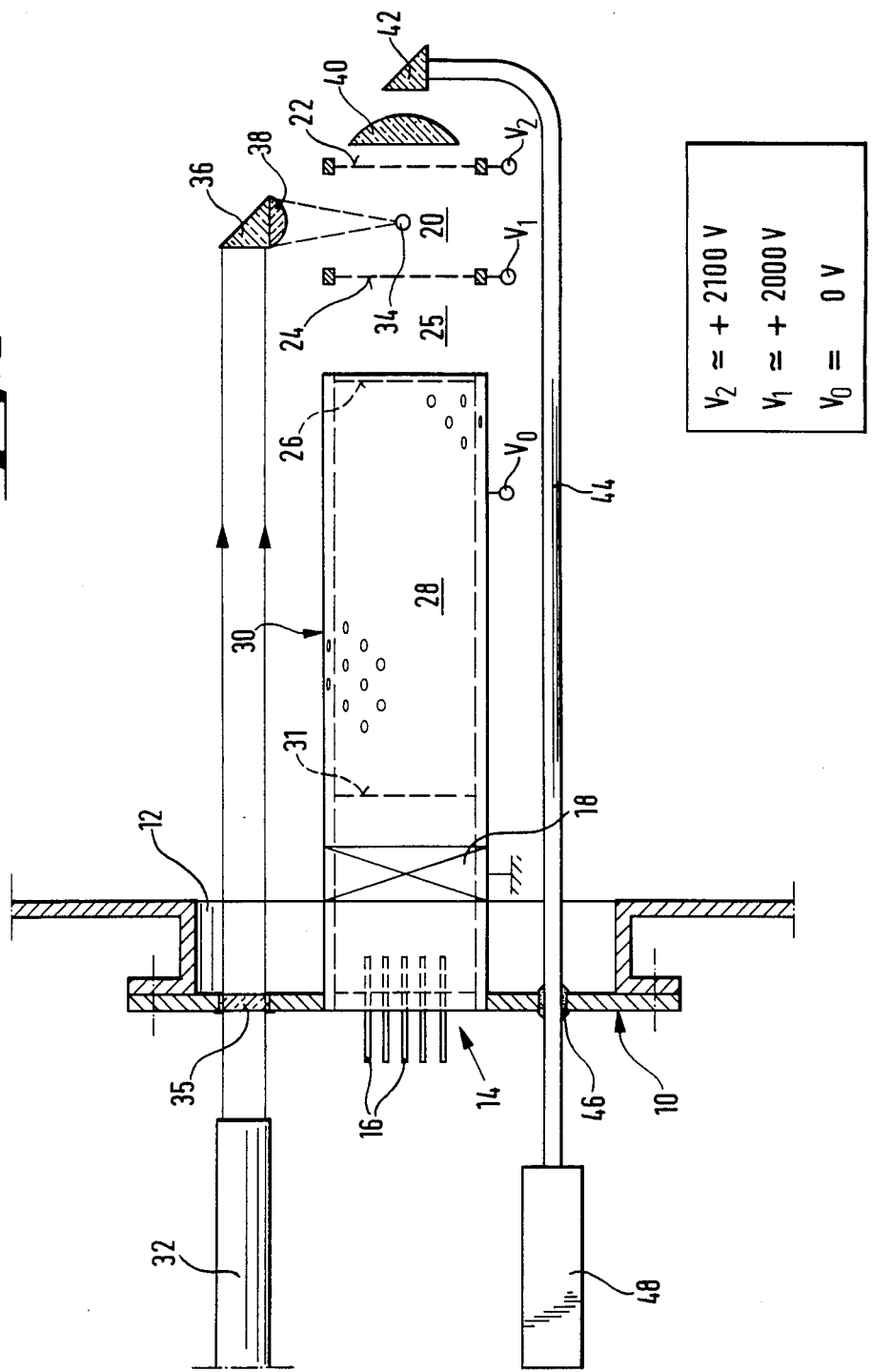

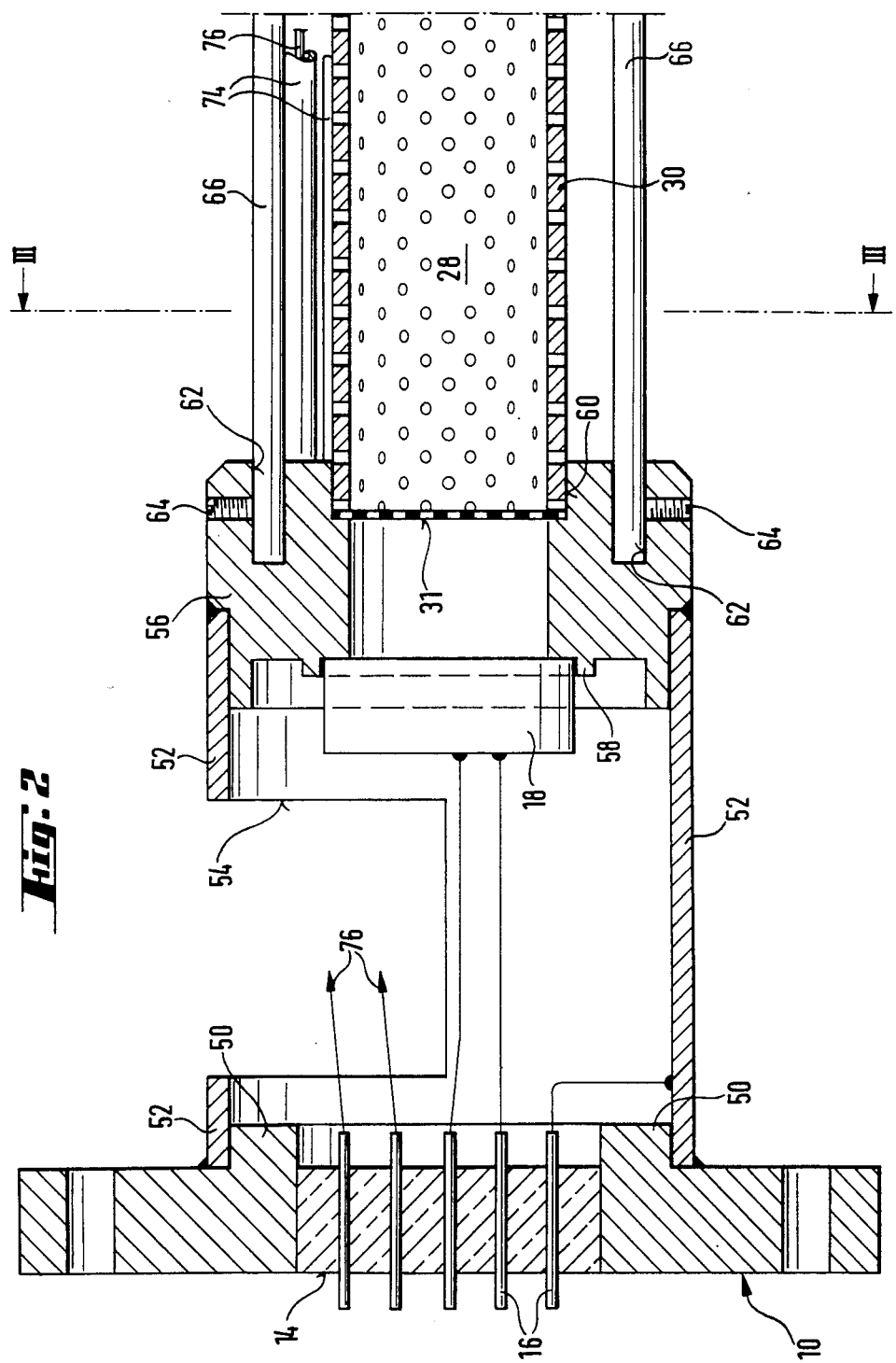

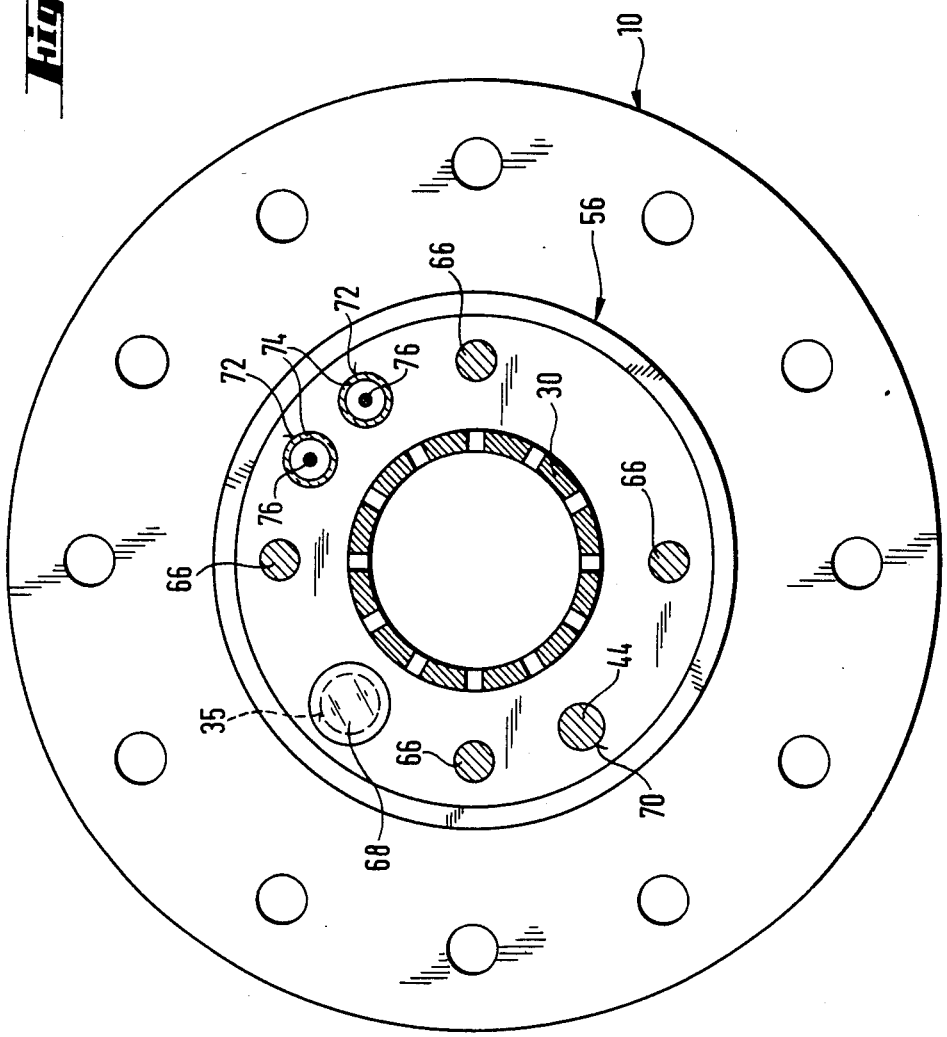

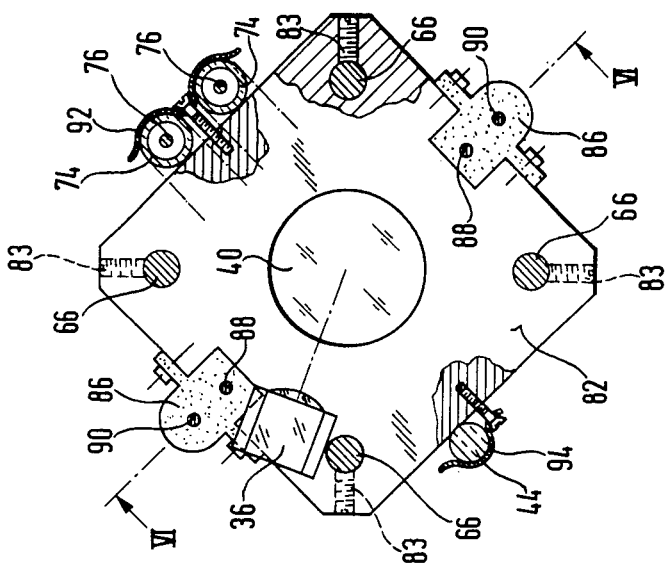
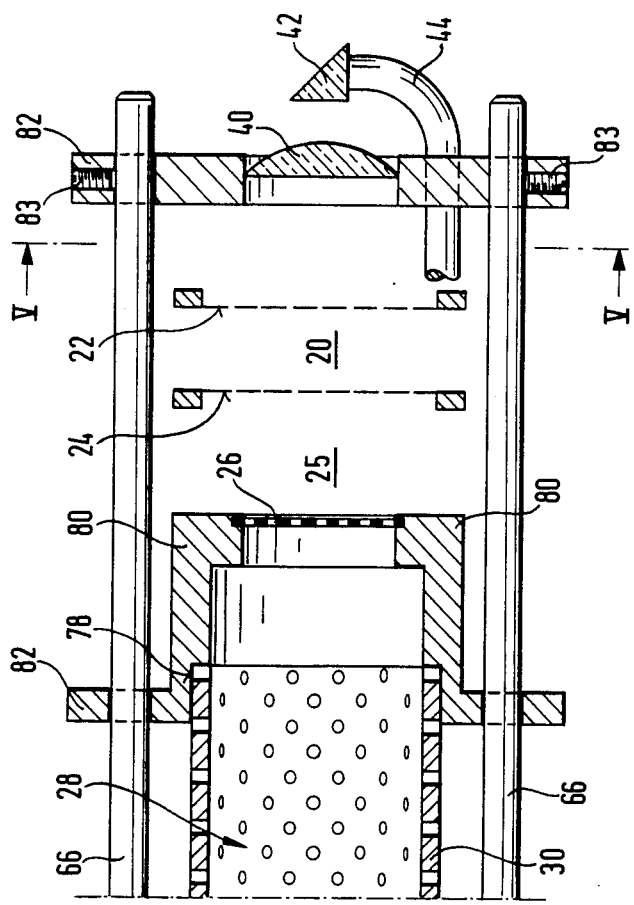

LASER MASS SPECTROMETER

The present invention relates to a mass spectrometer, more specifically a mass spectrometer in which a substance to be investigated is ionized by laser radiation.

A laser mass spectrometer of the type of interest is described in my publication "Ultrasensitive Finger Print-Detection of Organometallic Compounds by laser Multiphoton Ionisation Mass Spectrometry" Appl. Phys. Lett. 45 (11), Dec. 1, 1984, incorporated by reference and enclosed with the present application.

Mass spectrometers of this type generally comprise as main components along an axis in the order named an ionization space or chamber into which a laser radiation beam is focussed for ionizing a substance or substances to be investigated or detected, further an adjacent acceleration space or path for mass-dependent acceleration of the ions produced, then an essentially field-free time-of-flight or separation space, within which the ions with different e/m ratios (e=electric charge; m=mass) separate because of their different velocities, and a detector system for the separated ions. The ionization may be wavelength selective or inselective.

An essential deficency of the known laser mass spectrometers of this type is that they cannot be accomodated easily to systems of different configurations with which the mass spectrometers is to be used. More specifically, the distance between the place, where the ions are produced, and the port or mounting flange, which is provided at the vacuum vessel of the respective system or apparatus, with which the mass spectrometer is used, is quite different from apparatus to apparatus, and, up to this date, it was generally necessary to modify the apparatus to align it to an existing commercial mass spectrometer.

A further problem encountered with the known mass spectrometers is that molecular substances are often severely broken up in parts ("fragmented") by the ionizing radiation so that ions of parts of the original substance rather than the so-called "parent ion" are produced and detected.

It is further desirable, to obtain further information about the substance under investigation in addition to the mass spectrum.

The present invention solves or at least greatly alleviates these problems. According to a first aspect of the present invention, a mass spectrometer is provided, which comprises an electrode system and ion detector means both mounted on a support flange adapted to be sealed to a port of a vacuum apparatus. The electrode system defines an ionization space and an ion acceleration space and comprises an electrode surrounding a time-of-flight or travel time separation path. The ionization space, the acceleration space, the separation path and the ion detector means are arranged along an axis in the order named and mounted on the support flange which comprises electrically isolated lead-in conductors for electrical connection of the electrode system and the ion detector means. According to a preferred embodiment of the present invention, the electrode encompassing the separation path is mounted on axially extending support members so that it can be easily replaced by a similar electrode of different length.

According to another aspect of the present invention, the mass spectrometer is provided with a laser radiation source for providing the ionizing radiation, said laser radiation source being adapted to emit pulses of a duration in the order of picoseconds, preferably about 10 picoseconds or shorter, to avoid breaking up molecular substances under investigation.

According to still another aspect of the present invention, means is provided for coupling out radiation which is emitted from the substance under investigation when subjected to the ionizing radiation in the ionization space to gain optic-spectroscopic information in addition to the mass spectrum.

Further features, aspects and advantages of the invention will become apparent when reading the following description of a preferred embodiment thereof.

SHORT DESCRIPTION OF THE DRAWINGS

FIG. 1 is a simplified view of a laser mass spectrometer in accordance with the present invention;

FIG. 2 is an axial cross-section of a flange end of a preferred embodiment of the laser mass spectrometer according to the invention;

FIG. 3 is a view in the direction of the arrows III—III of FIG. 2;

FIG. 4 is an axial section of the ion source end of the mass spectrometer of FIG. 2;

FIG. 5 is a view in the direction of the arrows 5—5 of FIG. 4, and

Figure 6:
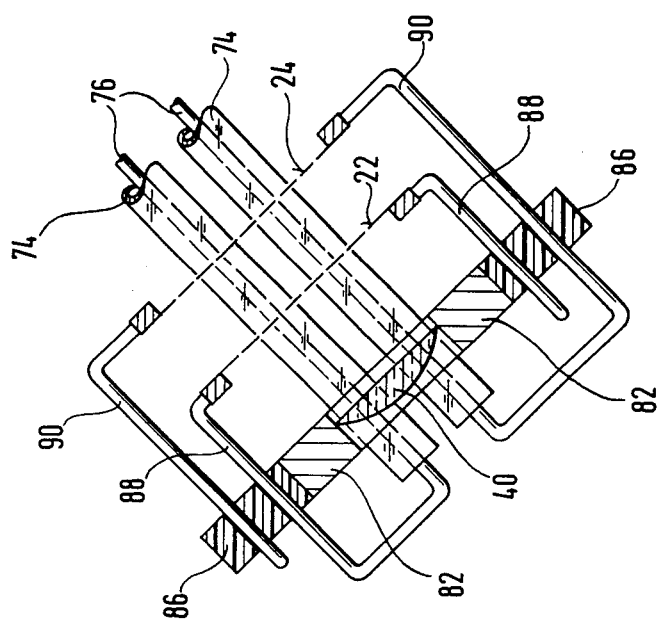
FIG. 6 is a section along the line VI—VI of FIG. 5.

As shown schematically in FIG. 1, a mass spectrometer according to the invention comprises a measuring system with a coupling flange 10 which allows to mount the measuring system in a vacuum-tight manner on a flanged port 12 of a vacuum system (not shown), in which a substance to be investigated by mass spectrometry is present or generated. It is a feature of the present laser mass spectrometer, that all parts of the measuring system are supported from the flange 10, thus, the measuring system protrudes in a cantilever fashion from the flange into the inner of the vacuum system. The flange 10 comprises electrical lead-in means 14 similar to an electron tube stem having a plurality of terminal pins 16. An ion detector system 18 is mounted adjacent the flange, said system comprising preferably a double channel-plate multiplier, i.e. a plate system having a multitude of small diameter channels operating as secondary electron multipliers. Such ion detectors are known and different types thereof are commercially available, thus, no further explanation will be necessary. In operation, a conventional electronic control and signal processing apparatus (not shown) is connected to the terminals 16 of the measuring system.

An ionization chamber or space 20 defined by a pair of parallel, plane grid or mesh electrodes 20, 24 having annular support rings is provided at the end of the measuring system remote from the mounting flange. A further grid or mesh electrode 26 which together with the electrode 24 defines an ion acceleration space 25 is provided on the detector side of the electrode 24 in spaced relationship therefrom. An essentially field-free separation or time-of-flight path 28 is provided between the electrode 26 and the ion detector 18. The path 18 is enclosed and shielded by an cylindrical electrode 30 made of thin, perforated sheet metal and has a grid or mesh electrode 31 at the end facing the flange 10. The electrodes 26 and 31 are electrically connected to the cylindrical electrode 30, so that the path 28 is free of electrical fields.

A laser 32 is provided for producing a radiation beam which is focussed into a focus region 34 within the ionization space. The laser may be a dye line, a frequency doubled dye laser or an excimer laser. Preferably, a synchroneously pumped dye laser in combination with an excimer laser-amplifier pumped by an argon laser is used, e.g. a dye laser of the type Coherent 599, a Lambda Physics type EMG 103 excimer laser, and an argon pump laser type CR18 are used to produce a radiation beam having a wave-length of 590 nanometers or if frequency doubling is used, a wave length of 295 nanometers. Lasers of this type are adapted to produce radiation pulses having a duration down to few picoseconds. This allows to detect also relatively instable molecules, as metalloorganic compounds and the like, without fragmentation (breaking up). While the laser radiation may be coupled into the vacuum system and the ionization space in a direction normal to the longitudinal axis of the mass spectrometer system through a window provided in the wall of the vacuum system with which the mass spectrometer is used, the preferred embodiment has an entrance window 35 in the mounting flange, and the laser beam travels first essentially parallel to the longitudinal axis of the mass spectrometer through the window to a prism 36 or another reflector which is provided on the side of the ionization space 20 and deflects the beam by 90°. The deflected beam is focussed by a lens 38 (which may be integrally formed with the prism 36) into the focus region 34 within the ionization space. Alternatively, a light guide system, as a light conducting fiber or rod or fibre bundle may be used for directing the laser radiation into the vacuum system and the ionization space.

The ions generated within the focus region 34 are transferred into the acceleration space 25 by a weak drift field typically of 100 volts between the electrodes 22 and 24, and then accelerated by an accelerating voltage of typically about 2000 volts between the electrodes 24 and 26. Since the acceleration of a charged particle by an electric field depends on the mass of the particle, more specifically to the ratio of e/m, as well known in the art, the ions enter the separation path 28 through the grid electrode 26 with velocities which are inverse proportional to the square root of the ratio of their charge e to their mass m. The ion with different values of e/m separate because of the different velocities when travelling along the path 28 and arrive therefore at the ion detector at different times after the radiation pulse by which they are generated. The principle of such time-of-flight mass spectrometers is well known in the art, thus, no further explanation is necessary.

According to an important aspect of the present invention, not only the ions produced in the focus region 34 are used for analyzing the substances which are present in the ionization space, but also the optical radiation, especially fluorescence radiation, emitted by the respective substances within the ionization space.

Thus, two different types of information can be simultaneously derived with a single laser radiation pulse ("shot"), i.e. mass spectrum information and optical-spectroscopic information. For this purpose, the optical radiation emitted from the excited substances within focus region 34 may be focussed by a lens 40 which may be a Fresnel lens, via a prism 42 into a light guide 44, e.g. a fibre bundle or monofilament light guide, which is lead out at 46 in a vacuum-tight manner through the flange 10 to the outside of the vacuum space, to apply the radiation to a spectroscopic apparatus 48 which separates the radiation on the basis of the wave-length by a diffraction grating or prism in a well known manner.

A preferred configuration of the mass spectrometer shown in FIG. 1 will now be described with reference to FIGS. 2 to 6. Same components are provided with the same reference numerals as in FIG. 1.

The vacuum or inner side of the flange 10 is provided with an annular boss 50, on which a metal tube 52 is mounted. The metal tube has a cut-out 54 on its one side. An annular body 56 is mounted on the end of the metal tube 52 remote from the flange 10. The surface of the body 56 facing the flange 10 forms seat means 58 for the ion detector 18. The seat means has an annular rib to accomodate ion detectors of different commercially available types. A seat 60 is formed on the side of the body 56 which is remote from the flange 10. The seat 60 receives the electrode 31 and supports one end of a perforated sheet metal tube which forms the electrode 30. Further, four holes are provided on this side, each receiving a support rod 66. Each support rod 66 is fixed in the respective hole 62 by a screw 64 which is shown only schematically.

As shown in FIG. 3, the body 56 has a window 68 through which the laser beam is projected and which is aligned with the window 35 (FIG. 1). Further, the body 56 has an aperture 70 for the light guide 44 (FIG. 1) and apertures 72 for electrical conductors 76 (FIG. 6) connecting to the electrodes 22 and 24. The conductors 76 are insulated by glass tubes 74 as best seen in FIGS. 5 and 6.

As shown in FIG. 4, the electrode 30, which surrounds the separation path 28, is seated with its end remote from the ion detector 18 in an annular recess 78 of a generally tube-shaped metal body 80, which is supported by an integral flange 82 on the rods 66. The flange 82 can be used for separating the vacuum space defined by a tubular part (not shown) of the envelope of the vacuum system surrounding the electrode system described and has apertures (not shown) for the conductors 76, the laser beam and the light guide 44. The opening of the metal body 80 which is remote from the separation path 28 is provided with a grid or mesh electrode 26.

All grid or mesh electrodes are preferably made of thin perforated nickel metal foils; the open area is as large as possible and may be in practice 80% and more.

An essentially square plate 82 of stainless steel is seated on the rods 66 near their ends. The rods traverse corresponding holes near the corners of the plate 82 and are fixed with respect to the plate by set screws 83. The plate has a center hole in which the lens 40 is seated. Insulating support members 86 are attached by screws on opposed edges of the plate 82. Each of said support members has two apertures for receiving bent support wires 88 and 90, respectively (FIG. 6) which are each connected to a corresponding conductor 76 and provide for mechanical support and electrical connection of the electrodes 22 and 24, respectively.

As shown in FIG. 5 the glass tubes 74 which insulate the conductors 76 are held to one side of the edge of the plate 22 by a spring clamp 92. A further spring clamp 94 is provided on the opposite side of the edge of the plate 92 for positioning the light guide 94. The prism 36 is supported on the plate 82 by appropriate uprights.

The above described embodiment of the mass spectrometer measuring system may have an outer diameter of about 63 mm, so that it fits easily through a mounting flange of an usual vacuum system. The system can be easily adapted to different situations: It has been found, that the length of the separation path 28 is not very critical and may vary between 20 cm and 100 cm and more without impairing the resolution of the time-of-flight mass spectrometer beyond a limit which is acceptable for many applications. Thus, the distance between the ionization space 20 and the mounting flange 10 can be easily adjusted by cutting the perforated sheet metal forming the electrode 30 to the desired length. The other components, as the rods 66, the glass tubes 74 and so on, the lengths of which may also have to be adjusted to the desired distance between the ionization space 20 and the mounting flange 10, can also be easily trimmed to the required length.

The electrodes 22, 24, 26, and 30 of the above-described preferred embodiment of the invention are made of nickel. The laser 32 of the preferred embodiment is a synchroneously pumped dye laser type Coherent 599 followed by an excimer laser amplifier type lambda Physics EMG103, pumped with an argon laser type Coherent CR18. The laser system 32 produces radiation pulses having a wavelength of about 590 nanometer (or if desired, after frequency doubling with a wavelength of 295 nanometers) and an energy in the order of microjoules to millijoules per pulse. The pulse length is about 10 picoseconds and may be even shorter, e.g. 2 picoseconds and less, to prevent an undue fragmentation of molecular substances to be analyzed and to allow the detection of the so-called parent ion. A pulse length of about 10 picoseconds has been found to be an acceptable compromise between costs and the detection sensitivity of the parent ion, since lasers for producing pulses with lengths in the order of few picoseconds are still rather expensive. If the detection of the parent ion is of lesser concern, longer pulse lengths up to e.g. 20 nanoseconds may be used; if the costs are of no concern, pulse lengths of 2 picoseconds and less are preferred.

Various modifications of the disclosed embodiment will occur to those skilled in the art without departing from the scope of the invention as defined by the appendet claims. Thus, the electrode 22 may be affixed to and supported by the plate 82. Tube support members may be used instead of the relatively thin solid rods 66, and the conductors for connecting the electrodes may extend through these tubes which may consist of an insulating material, as ceramic. The electrodes 22 and 24 may be attached to the ends of an insulating tube or may each be mounted on an individual stainless steel plate corresponding to the plate 82; in this case the mounting wires 88 and 90 may be offset by 90 degrees or mounted on individual support members 86 mounted on different sides of the respective plates.

I claim:

1. A mass spectrometer comprising an electrode system (22, 24, 26, 30), which defines an ionization space (20) and an ion accelerating space (25) and which includes an electrode (30) surrounding a time-of-flight separation path (28), said ionization space (20), said acceleration space (25) and said separation path (28) being arranged in the order named along an axis; further comprising electron detector means (18) positioned at an end of said separation path (28) remote from said accelaration space (25); and a mounting flange (10) provided with electrical lead-through means (16) for electrical connection of the electrodes of the electrode system and of the ion detector means, characterized in that at least said electrode (30) which surrounds said separation path (28) is mounted in an easily removable manner on support members (66) extending in axial direction along said electrode system.

2. The mass spectrometer as claimed in claim 1 wherein all of the electrodes of said electrode system and said ion detecting means are supported in a cantilever fashion from said mounting flange (10).

3. The mass spectrometer as claimed in claim 1 wherein said ionization space (20) is provided at the end of said separation path (28) remote from said mounting flange (10).

4. The mass spectrometer as claimed in claim 1 wherein said electrode (30) surrounding said separation path (28) has a tubular shape and is supported with its ends in seat means (60, 78) formed by annular bodies (56, 80), at least one (80) of said bodies being mounted in an easily removable manner on said support members (66).

5. The mass spectrometer as claimed in claim 1 wherein a least one of a pair of electrodes (22, 24) defining said ionization space (20) is mounted on electrical conductors (88, 90), which in turn are mounted axially adjustably on mounting members (66) supported by a removable support body (82).

6. A mass spectrometer as claimed in claim 1 wherein said mounting members (66) have ends facing said mounting flange (10) removably mounted on an annular body (56), said annular body being mounted on said support flange (10) by means of a tubular member (52) having a lateral aperature (54).

7. A mass spectrometer as claimed in claim 6 wherein said annular body (56) forms seat means (58) for said ion detecting means (18) on its side facing said mounting flange (10).

8. The mass spectrometer as claimed in claim 1, wherein said mounting members are axially extending rod-shaped members (66).

9. The mass spectrometer as claimed in claim 1, wherein said support members are axially extending tubes.

10. The mass spectrometer as claimed in claim 1, characterized by means (36, 38) allowing an ionizing radiation to enter said ionization space (20) through said mounting flange (10).

11. The mass spectrometer as claimed in claim 1, characterized by means (40, 42, 44) for coupling radiation out of said ionization space (20).

12. The mass spectrometer as claimed in claim 11, wherein said coupling-out means (40, 42, 44) is adapted to guide said radiation through said mounting flange (10).

13. A mass spectrometer having an electrode system defining an ionization space, an ion acceleration space, ion separation means and ion detector means positioned in the order named along an ion path; further compromising laser means for ionizing a substance to be detected within said ionization space, said laser means providing a laser beam propagating through said ionization space along a predetermined direction; means for coupling out optical radiation emitted by the substance in the ionization space along an optical path which crosses the laser beam direction within said ionization space, said optical path being coupled to a spectroscopic apparatus for separating said radiation according to wavelength.

14. A mass spectrometer comprising
means for forming an ionization space;
laser means for producing laser radiation pulses directed into said ionization space to ionize a substance to be investigated;

means for accelerating ions produced in said ionization space;

means for separating the accelerated ions on the basis of their charge-to-mass ratio; and means for detecting the separated ions, the improvement consisting in that said laser means is adapted to produce radiation pulses of a length of no more than about 10 picoseconds to avoid undue fragmentation of the substance to be investigated.

15. The mass spectrometer as claimed in claim 1 further comprising laser means for producing a laser beam directed into said ionization space, said laser means being adapted to produce radiation pulses of a duration of no more than about 10 picoseconds.

16. The mass spectrometer as claimed in claim 1, wherein said electrode surrounding said separation path is made of a piece of perforeted thin sheet metal.

* * * * *